United States Patent [19]

DeForrest

[11] Patent Number: 4,819,340

[45] Date of Patent: Apr. 11, 1989

[54] COMPACT FOCAL PLANE PRECISION POSITIONING DEVICE AND METHOD

[75] Inventor: Allen L. DeForrest, Santa Ynez, Calif.

[73] Assignee: The United States of America as represented by the Secretary of the Air Force, Washington, D.C.

[21] Appl. No.: 124,640

[22] Filed: Nov. 24, 1987

[51] Int. Cl.$^4$ .............................................. G01B 5/00
[52] U.S. Cl. ....................................... 33/613; 33/568; 33/573; 33/DIG.13; 33/790
[58] Field of Search ................. 33/568, 573, DIG. 13, 33/613, 163, 125 R

[56] References Cited

U.S. PATENT DOCUMENTS

| | | | |
|---|---|---|---|
| 1,421,935 | 7/1922 | Gilbert . | |
| 1,798,955 | 3/1931 | Schwerin . | |
| 2,681,566 | 6/1954 | Ruge | 33/DIG. 13 |
| 2,761,216 | 9/1956 | Gollub | 33/DIG. 13 |
| 3,690,160 | 9/1972 | Kriesten . | |
| 4,279,164 | 7/1981 | Hawke et al. . | |
| 4,335,615 | 6/1982 | Kalfa et al. . | |
| 4,475,403 | 10/1984 | Lentz . | |

Primary Examiner—Harry N. Haroian
Attorney, Agent, or Firm—Donald J. Singer; Robert L. Nathans

[57] ABSTRACT

Method of precisely positioning a first terminal portion of an elongated tensile rod with respect to a base member coupled to a second terminal portion of the tensile rod which has a threaded portion, involves providing an electrical strain gage measurement device affixed to the tensile rod, a load tube positioned about the rod, having a first terminal portion positioned against the base member, and tightening a nut member over the threaded portion of the rod and against the load tube for producing compression of the tube and tension within the rod until a signal produced by the strain gage measuring device indicates a desired position of a terminal portion of the rod with respect to the base member.

20 Claims, 1 Drawing Sheet

COMPACT FOCAL PLANE PRECISION POSITIONING DEVICE AND METHOD

STATEMENT OF GOVERNMENT INTEREST

The invention described herein may be manufactured and used by or for the Government for governmental purposes without the payment of any royalty thereon.

BACKGROUND OF THE INVENTION

The present invention relates to the field of precision positioning devices. Certain objects such as optical focal planes require extremely accurate axial positional placement. In the past, this was accomplished by mechanical preloading of support assemblies for such focal planes and utilizing bulky mechanical force gages for accomplishing such preloading.

SUMMARY OF THE INVENTION

It is thus an object of the present invention to provide a method of eliminating such force gages by utilizing a novel, compact, space-saving arrangement for precisely measuring such preloading and hence positioning of an object in a more convenient manner.

The preferred method of the invention involves providing an electrical strain gage measurement means affixed to a threaded tensile member, and a load tube, positioned about the tensile member having a first terminal portion positioned against a base member. A nut member positioned upon the threaded portion of the tensile member, induces greater and greater compression of the tube and tension within the tensile member until a signal produced by the strain gage measuring means indicates a desired position of the first terminal portion of the tensile member with respect to the base member.

BRIEF DESCRIPTION OF THE DRAWINGS

Other objects, features and advantages of the present invention will become apparent upon study of the following detailed description taken in conjunction with the drawings in which.

DETAILED DESCRIPTION OF A PREFERRED EMBODIMENT

Figure 1:
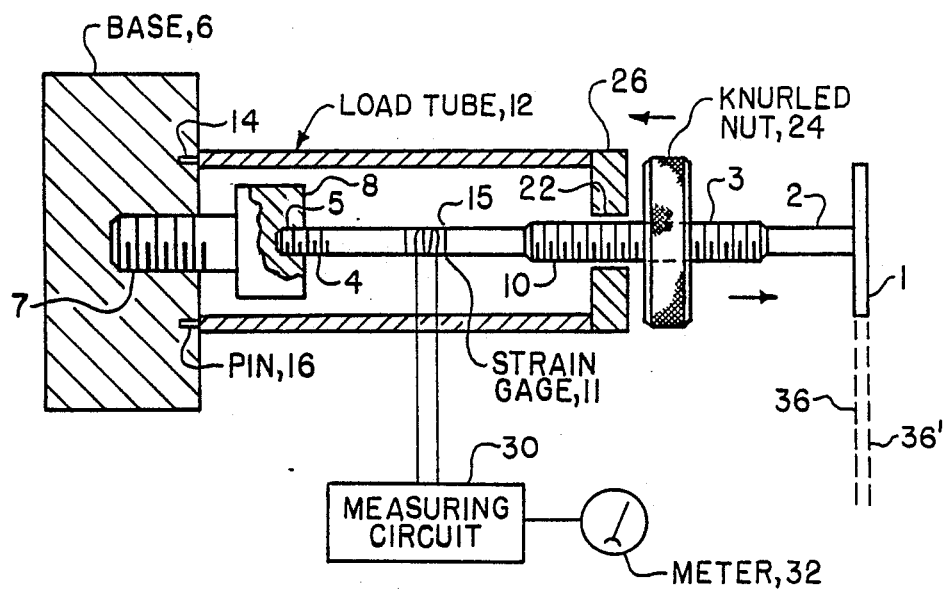
FIG. 1 illustrates a preferred embodiment of the present invention illustrated in cross section.

As illustrated in FIG. 1, an object to be positioned 1, is rigidly coupled to a first terminal portion 2 of an elongated tensile member 3. A second threaded terminal portion 4 is screwed into a threaded orifice 5 formed within a threaded member 8 which is in turn screwed within base member 6 at threaded cavity 7. Elongated tensile member 3 also has a threaded portion 10, positioned between a strain gage receiving portion 15 and first terminal portion 2. Cylindrical loading tube or compression member 12 has an anti-rotation device upon its first terminal portion such as pins 14 and 16, which in turn are fitted within pin-receiving holes in base 6. Cylindrical loading tube 12 has a second terminal portion including a plastic washer 16 which is affixed to the cylindrical walls of loading tube 12. A cylindrical orifice 22 is utilized to receive threaded portion 10 of the elongated tensile member 3. The right-hand first terminal portion 2 of the elongated tensile member is utilized to establish the exact axial position of a device 1 such as a focal plane. Focal plane 1 is rigidly affixed to the first terminal portion of the tensile member after the components are assembled.

Coarse positioning of the right-hand terminal portion of tensile member 3 is accomplished by rotating the coarse positioning screw 8 with respect to the threaded hole formed within base member 6. At this time, the object 1 is not affixed to the right-hand portion of tensile member 3 so that loading tube 12 may be readily slipped over the tensile member, since its orifice 22 has a greater diameter than threaded portion 10 of tensile member 3. The anti-rotation pins 14 and 16 are fitted within base member 6 and a knurled nut 24 is rotated about threaded portion 10 until it is firmly positioned against the right-hand surface of the plastic washer device 26. Conventional strain gage transducer 11 preferably made of fine wire, zig-zaged in the usual manner, is bonded to member 3, and is electrically coupled to the input circuit of a current measuring bridge circuit 30, which in turn is coupled to output meter 32. The function of the strain gage measurement means comprising elements 11, 30 and 32, is to measure the degree of tension induced into elongated tensile member 3 by virtue of further rotation of nut member 24 which places the cylindrical walls of loading tube 12 in compression, and elongated tensile member 3 in tension. Upon further rotation of nut 24, the right-hand terminal portion of element 3 will be shifted to the right, owing to the increased tension, and the resulting increased strain, induced within member 3. The reading of meter 32 will indicate the degree of tension induced within elongated member 3 which in turn is a known function of the axial position of the terminal portion of element 3, after calibration is carried out. Thus, observation of the output signal from the strain gage measurement means, is a convenient method of remotely reading the exact shift in position of the right-hand portion of elongated tensile member 3, with respect to the initial position plane 36, established by the aforesaid rotation of the threaded screw member 8, before the rotation of nut 24 against washer 26 produces the aforesaid compression of cylindrical loading tube 12. With this arrangement, the compressive strain within the walls of cylindrical loading tube 12 will be less than the tensile strain induced in the central portions of elongated tensile member 3 to cause device 1 to be displaced small distances to the right as nut 24 continues to press against washer 26 upon further rotation thereof. The new position of device 11, which could be a focal plane, is represented at 36'.

Figure 2:
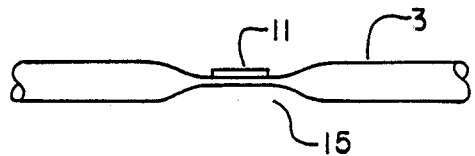
FIG. 2 illustrates a portion of the elongated tensile member.

As shown in FIG. 2, the thickness of strain gage receiving portion 15 is considerably reduced to facilitate motion of the first terminal tube portion, and hence the object mounted thereon, to the right. In the working prototype of the invention, the diameter of cylindrical member 3 was 0.135 inches, the length of the strain gage receiving portion 15 was 0.15 inches and the thickness of portion 15 was 0.065 inches. The bonded strain gage utilized, is of the conventional variety and is affixed to elongated element 3 by bonding in the usual manner. The strain gage measurement means are well-known in the art and thus will not be further described. See pages 187 and 188 of Volume 13 of the McGraw-Hill Encyclopedia of Science and Technology; 1977.

Having described specific embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. Method of precisely positioning a first terminal portion of an elongated tensile member with respect to a base member coupled to a second terminal portion of said tensile member, said tensile member having a threaded portion and a strain gage receiving portion, comprising the steps of:

providing an electrical strain gage measurement means affixed to said strain gage receiving portion of said tensile member, a load tube positioned about said tensile member having a first terminal portion positioned against said base member, and a second terminal portion having a tensile member receiving orifice with a cross-sectional area greater than the cross-sectional area of the threaded portion of said tensile member positioned therein; and tightening a nut member over the threaded portion of said tensile member and against said second terminal portion of said load tube for producing compression of said tube and tension within said tensile member until a signal produced by said strain gage measuring means indicates a desired position of the first terminal portion of said tensile member with respect to said base member.

2. The method of claim 1 wherein said second terminal portion of said load tube has a low friction bearing surface for facilitating rotation of said nut member contacting said second terminal portion of said load tube.

3. The method of claim 1 wherein the strain gage receiving portion of said tensile member has a greatly reduced thickness with respect to remaining portions of said tensile member.

4. The method claim 2 wherein the strain gage receiving portion of said tensile member has a greatly reduced thickness with respect to remaining portions of said tensile member.

5. The method of claim 1 further including rotating a screw member coupled between said base member and the second terminal portion of said tensile member for coarse positioning of the first terminal portion of said tensile member.

6. The method of claim 2 further including rotating a screw member coupled between said base member and the second terminal portion of said tensile member for coarse positioning of the first terminal portion of said tensile member.

7. The method of claim 3 further including rotating a screw member coupled between said base member and the second terminal portion of said tensile member for coarse positioning of the first terminal portion of said tensile member.

8. The method of claim 4 further including a rotating screw member coupled between said base member and the second terminal portion of said tensile member for coarse positioning of the first terminal portion of said tensile member.

9. The method of claim 1 wherein said nut member is knurled for facilitating manual rotation thereof.

10. The method of claim 5 wherein said nut member is knurled for facilitating manual rotation thereof.

11. The method of claim 6 wherein said nut member is knurled for facilitating manual rotation thereof.

12. The method of claim 8 wherein said nut member is knurled for facilitating manual rotation thereof.

13. A device for precisely positioning a first terminal portion of an elongated tensile member with respect to a base member coupled to a second terminal portion of said tensile member, said tensile member having a threaded portion, and a strain gage receiving portion having an electrical strain gage measurement means thereon, a load tube, positioned about said tensile member, with a first terminal tube portion positioned against said base member, and a second terminal tube portion positioned about the threaded portion of said tensile member, and a nut member, mounted upon the threaded portion of said tensile member and positionable against said second terminal portion of said load tube, for producing compression of said tube and tension within said tensile member, to enable said measurement means to produce a signal indicative of the position of the first terminal portion of said tensile member with respect to said base member.

14. The device of claim 13 further including a screw member coupled between said base member and the second terminal portion of said tensile member for coarse positioning of the first terminal portion of said tensile member.

15. The device of claim 13 further including anti-rotation means positioned upon said first terminal tube portion.

16. The device of claim 14 further including anti-rotation means positioned upon said first terminal tube portion.

17. The device of claim 13 further including a focal plane platen affixed to the first terminal portion of said tensile member.

18. A device for precisely positioning a first terminal portion of an elongated tensile member with respect to a base member coupled to a second terminal portion of said tensile member, said tensile member having a strain gage receiving portion with an electrical strain gage measurement means thereon, a compression member having a first terminal position positioned against said base member, and a second portion coupled to said tensile member, and means for producing compression within said compression member and tension within said tensile member, to enable said measurement means to produce a signal indicative of the position of the first terminal portion of said tensile member with respect to said base member.

19. The device of claim 18 further including a screw member coupled between said base member and the second terminal portion of said tensile member for coarse positioning of the first terminal portion of said tensile member.

20. The device of claim 16 further including a focal plane platen affixed to the first terminal portion of said tensile member.

* * * * *